United States Patent
Li

(10) Patent No.: US 10,869,607 B2
(45) Date of Patent: Dec. 22, 2020

(54) APPARATUS AND METHOD FOR DETERMINING A BLOOD PRESSURE OF A SUBJECT

(71) Applicant: BOE TECHNOLOGY GROUP CO., LTD., Beijing (CN)

(72) Inventor: Hui Li, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 505 days.

(21) Appl. No.: 15/565,361

(22) PCT Filed: Oct. 20, 2016

(86) PCT No.: PCT/CN2016/102712
§ 371 (c)(1),
(2) Date: Oct. 9, 2017

(87) PCT Pub. No.: WO2018/072175
PCT Pub. Date: Apr. 26, 2018

(65) Prior Publication Data
US 2018/0303354 A1   Oct. 25, 2018

(51) Int. Cl.
*A61B 5/021* (2006.01)
*A61B 5/0452* (2006.01)
(Continued)

(52) U.S. Cl.
CPC ........ *A61B 5/02125* (2013.01); *A61B 5/0261* (2013.01); *A61B 5/0295* (2013.01);
(Continued)

(58) Field of Classification Search
CPC ....... A61B 5/021; A61B 5/026; A61B 5/0295; A61B 5/0456; A61B 5/0261;
(Continued)

(56) References Cited

U.S. PATENT DOCUMENTS 6,027,455 A * 2/2000 Inukai ................ A61B 5/02125
600/485
2012/0078123 A1   3/2012 Futatsuyama et al.
(Continued)

FOREIGN PATENT DOCUMENTS

CN   102397064 A *   4/2012
CN   102894964 A     1/2013
(Continued)

OTHER PUBLICATIONS

International Search Report & Written Opinion dated Jul. 19, 2017, regarding PCT/CN2016/102712.

*Primary Examiner* — Eric J Messersmith
(74) *Attorney, Agent, or Firm* — Intellectual Valley Law, P.C.

(57) ABSTRACT

The present application discloses an apparatus for determining a blood pressure of a subject, the apparatus includes a sensor assembly configured to measure a pulse wave signal of the subject; and a signal processor configured to generate a metric of the pulse wave signal based on the pulse wave signal, to select a blood pressure calculation algorithm base on the metric of the pulse wave signal, and to determine the blood pressure of the subject using the blood pressure calculation algorithm.

18 Claims, 8 Drawing Sheets

(51) Int. Cl.
*A61B 5/00* (2006.01)
*A61B 5/024* (2006.01)
*A61B 5/026* (2006.01)
*A61B 5/0295* (2006.01)
*A61B 5/0456* (2006.01)
*A61B 5/022* (2006.01)
*A61B 5/11* (2006.01)

(52) U.S. Cl.
CPC ........ *A61B 5/02416* (2013.01); *A61B 5/0452* (2013.01); *A61B 5/0456* (2013.01); *A61B 5/6824* (2013.01); *A61B 5/6828* (2013.01); *A61B 5/7257* (2013.01); *A61B 5/7278* (2013.01); *A61B 5/02225* (2013.01); *A61B 5/1112* (2013.01); *A61B 5/746* (2013.01); *A61B 2560/0214* (2013.01); *A61B 2560/0223* (2013.01); *A61B 2562/043* (2013.01)

(58) Field of Classification Search
CPC . A61B 5/7278; A61B 5/6828; A61B 5/02125; A61B 5/02416; A61B 5/0452; A61B 5/6824; A61B 5/7257; A61B 5/746; A61B 5/02225; A61B 5/1112; A61B 2560/0214; A61B 2560/0223; A61B 2562/043
See application file for complete search history.

(56) References Cited

U.S. PATENT DOCUMENTS

| | | | |
|---|---|---|---|
| 2014/0073874 | A1 | 3/2014 | Rodriguez-Llorente et al. |
| 2016/0242700 | A1* | 8/2016 | Ferber .................. A61B 5/7278 |
| 2017/0109495 | A1 | 4/2017 | Xin |
| 2017/0245767 | A1* | 8/2017 | Ferber ................ A61B 5/02108 |
| 2018/0279965 | A1* | 10/2018 | Pandit .................. A61B 5/7225 |

FOREIGN PATENT DOCUMENTS

| | | |
|---|---|---|
| CN | 104739395 A | 7/2015 |
| CN | 105748051 A | 7/2016 |
| WO | 2015161688 A1 | 10/2015 |

* cited by examiner

A

B

APPARATUS AND METHOD FOR DETERMINING A BLOOD PRESSURE OF A SUBJECT

CROSS-REFERENCE TO RELATED APPLICATION

This application is a national stage application under 35 U.S.C. § 371 of International Application No. PCT/CN2016/102712, filed Oct. 20, 2016, the contents of which are incorporated by reference in the entirety.

TECHNICAL FIELD

The present invention relates to an apparatus and a method for determining a blood pressure of a subject.

BACKGROUND

Conventional blood pressure measurement apparatuses include sphygmomanometer, oscillometry, and invasive vascular pressure monitoring. Blood pressure measurement using a sphygmomanometer is based on Korotkoff sound. Typically, a sphygmomanometer includes a stethoscope and a cuff. Oscillometry includes a cuff and electronics to determine the blood pressure based on cuff pressure oscillations. The invasive vascular pressure method involves placing a cannula needle or catheter into an artery. These conventional methods are either invasive or cumbersome.

SUMMARY

In one aspect, the present invention provides an apparatus for determining a blood pressure of a subject, comprising a sensor assembly configured to measure a pulse wave signal of the subject; and a signal processor configured to generate a metric of the pulse wave signal based on the pulse wave signal, to select a blood pressure calculation algorithm base on the metric of the pulse wave signal, and to determine the blood pressure of the subject using the blood pressure calculation algorithm.

Optionally, the signal processor is configured to perform one or more of time domain analysis, frequency domain analysis, time-frequency domain analysis on the pulse wave signal of the subject; wherein the metric comprises one or more of a metric in time domain of the pulse wave signal, a metric in frequency domain of the pulse wave signal, and a metric in time-frequency domain of the pulse wave signal.

Optionally, the metric in time domain of the pulse wave signal comprises one or more of a ratio between amplitudes at two reference points in the time domain of the pulse wave signal; a ratio between $\Delta t1$ and $\Delta t2$ in the time domain of the pulse wave signal, wherein $\Delta t1$ is a first time difference between a first pair of reference points, and $\Delta t2$ is a second time difference between a second pair of reference points; a ratio between S1 and S2, wherein S1 is a first area defined by a first pair of reference points under a curve of a time domain representation of the pulse wave signal, and S2 is a second area defined by a second pair of reference points under the curve of the time domain representation of the pulse wave signal.

Optionally, the metric in frequency domain of the pulse wave signal comprises a plurality of frequencies with highest energy levels.

Optionally, the metric in time-frequency domain of the pulse wave signal comprises a correlation between a frequency domain metric and a time domain metric.

Optionally, the signal processor is configured to calculate a pulse wave velocity of the subject based on the pulse wave signal measured by the sensor assembly; compare the metric of the pulse wave signal with a plurality of reference metrics of a plurality of reference pulse wave signals; select the blood pressure calculation algorithm from a plurality of reference blood pressure calculation algorithms associated with the plurality of reference pulse wave signals, respectively, based on a result of the comparing; and determine the blood pressure of the subject using the pulse wave velocity of the subject and the selected blood pressure calculation algorithm.

Optionally, the sensor assembly comprises an electrocardiography sensor configured to measure an electrocardiography R-wave and a pulse wave sensor configured to measure an arterial pulse wave; the signal processor is configured to calculate a time difference between the electrocardiography R-wave and the arterial pulse wave as a pulse transit time.

Optionally, the sensor assembly comprises at least two pulse wave sensors configured to measure arterial pulse waves at least two arterial sites; the signal processor is configured to calculate a time difference between the two arterial pulse waves as a pulse transit time.

Optionally, the apparatus further comprises a memory having a database comprising the plurality of reference metrics corresponding to the plurality of reference blood pressure calculation algorithms; wherein the plurality of reference metrics comprises one or more of a metric in time domain of a reference pulse wave signal, a metric in frequency domain of a reference pulse wave signal, and a metric in time-frequency domain of a reference pulse wave signal.

Optionally, the blood pressure calculation algorithm is derived from a prediction model established using a plurality of reference metrics of a plurality of reference pulse wave signals.

Optionally, the signal processor is configured to select the prediction model from a plurality of reference prediction models established for a plurality of subpopulations, respectively.

Optionally, the prediction model is established using an ordinary least squares regression method.

Optionally, the apparatus further comprises an analog-to-digital converter configured to convert the pulse wave signal measured by the sensor assembly into digital data, and transmit the digital data to the signal processor for analysis; a user interface configured to display information and for the user to input data to the apparatus; a power supply configured to provide power to the apparatus; and a memory configured to store the digital data, the plurality of reference metrics, the plurality of reference blood pressure calculation algorithms, and the plurality of reference pulse wave signals.

Optionally, the apparatus is a wearable apparatus.

In another aspect, the present invention provides a method of determining a blood pressure of a subject, comprising measuring a pulse wave signal of the subject; generating a metric of the pulse wave signal; and determining the blood pressure of the subject using a blood pressure calculation algorithm.

Optionally, the method further comprises performing one or more of time domain analysis, frequency domain analysis, time-frequency domain analysis; wherein the metric comprises one or more of a metric in time domain of the pulse wave signal, a metric in frequency domain of the pulse wave signal, and a metric in time-frequency domain of the pulse wave signal.

Optionally, the metric in time domain of the pulse wave signal comprises one or more of a ratio between amplitudes at two reference points in the time domain of the pulse wave signal; a ratio between Δt1 and Δt2 in the time domain of the pulse wave signal, wherein Δt1 is a first time difference between a first pair of reference points, and Δt2 is a second time difference between a second pair of reference points; a ratio between S1 and S2, wherein S1 is a first area defined by a first pair of reference points under a curve of a time domain representation of the pulse wave signal, and S2 is a second area defined by a second pair of reference points under the curve of the time domain representation of the pulse wave signal.

Optionally, the metric in frequency domain of the pulse wave signal comprises a plurality of frequencies with highest energy levels.

Optionally, the metric in time-frequency domain of the pulse wave signal comprises a correlation between a frequency domain metric and a time domain metric.

Optionally, the method further comprises calculating a pulse wave velocity of the subject; comparing the metric of the pulse wave signal with a plurality of reference metrics of a plurality of reference pulse wave signals; selecting the blood pressure calculation algorithm from a plurality of reference blood pressure calculation algorithms associated with the plurality of reference pulse wave signals, respectively, based on a result of the comparing; and determining the blood pressure of the subject using the pulse wave velocity of the subject and the blood pressure calculation algorithm.

Optionally, the step of calculating the pulse wave velocity comprises calculating a time difference between an electrocardiography R-wave and an arterial pulse wave as a pulse transit time.

Optionally, the method further comprises establishing a database comprising the plurality of reference metrics corresponding to the plurality of reference blood pressure calculation algorithms; wherein the plurality of reference metrics comprises one or more of a metric in time domain of a reference pulse wave signal, a metric in frequency domain of a reference pulse wave signal, and a metric in time-frequency domain of a reference pulse wave signal.

Optionally, the method further comprises updating the database.

Optionally, the blood pressure calculation algorithm is derived from a prediction model established using a plurality of reference metrics of a plurality of reference pulse wave signals.

Optionally, the method further comprises selecting the prediction model from a plurality of reference prediction models established for a plurality of subpopulations, respectively.

Optionally, the prediction model is established using an ordinary least squares regression method.

BRIEF DESCRIPTION OF THE FIGURES

The following drawings are merely examples for illustrative purposes according to various disclosed embodiments and are not intended to limit the scope of the present invention.

DETAILED DESCRIPTION

Figure 1:
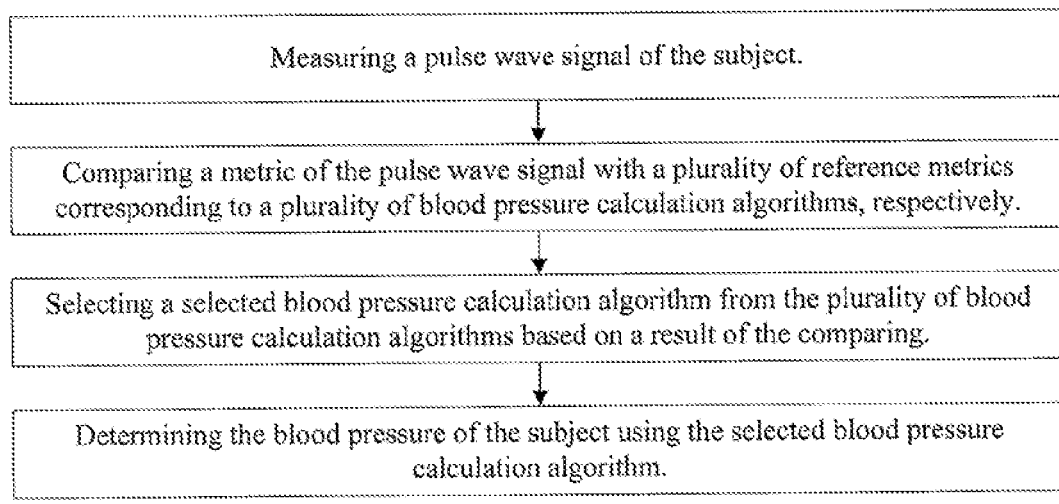
FIG. 1 is a flow chart illustrating a method for determining a blood pressure of a subject in some embodiments according to the present disclosure.

The disclosure will now be described more specifically with reference to the following embodiments. It is to be noted that the following descriptions of some embodiments are presented herein for purpose of illustration and description only. It is not intended to be exhaustive or to be limited to the precise form disclosed.

Non-invasive and cuff-less blood pressure methods and apparatuses have become a focus of research and development in recent years. Currently, there is no known cuff-less, non-invasive method that can accurately and reliably measure a subject's blood pressure, e.g., providing a blood pressure measurement comparable to that measured by sphygmomanometer and oscillometry. The present invention provides, inter alia, an apparatus and an accurate, reliable, and non-invasive method for determining a blood pressure of a subject that substantially obviate one or more of the problems due to limitations and disadvantages of the related art. In one aspect, the present disclosure provides an apparatus for determining a blood pressure of a subject. In some embodiments, the apparatus includes a sensor assembly configured to measure a pulse wave signal of the subject; and a signal processor configured to generate a metric of the pulse wave signal, to select a blood pressure calculation algorithm, and to determine the blood pressure of the subject using the blood pressure calculation algorithm. In another aspect, the present disclosure provides a method of determining a blood pressure of a subject. In some embodiments, the method includes measuring a pulse wave signal of the subject; generating a metric of the pulse wave signal; and determining the blood pressure of the subject using a blood pressure calculation algorithm. In some embodiments, the metric of the pulse wave signal measured by the sensor assembly is one or more of a metric in time domain of the pulse wave signal, a metric in frequency domain of the pulse wave signal, and a metric in time-frequency domain of the pulse wave signal.

Various appropriate blood pressure calculation algorithms may be used for determining the blood pressure of the subject. In one example, the blood pressure calculation algorithm may be selected by comparing the metric of the pulse wave signal with a plurality of reference metrics of a plurality of reference pulse wave signals; selecting the blood pressure calculation algorithm from a plurality of reference blood pressure calculation algorithms associated with the plurality of reference pulse wave signals, respectively, based on a result of the comparing; and determining the blood pressure of the subject using the pulse wave velocity of the subject and the blood pressure calculation algorithm. In another example, the blood pressure calculation algorithm may be derived from a prediction model established using a plurality of reference metrics of a plurality of reference pulse wave signals, i.e., the metric of the pulse wave signal measured from the subject is compared with the plurality of reference metrics of the plurality of reference pulse wave signals by way of the prediction model.

FIG. 1 is a flow chart illustrating a method for determining a blood pressure of a subject in some embodiments according to the present disclosure. Referring to FIG. 1, the method in the embodiment includes measuring a pulse wave signal of the subject; comparing a metric of the pulse wave signal with a plurality of reference metrics of a plurality of reference pulse wave signals; selecting a blood pressure calculation algorithm from a plurality of reference blood pressure calculation algorithms associated with the plurality of reference pulse wave signals, respectively, based on a result of the comparing; and determining the blood pressure of the subject using the selected blood pressure calculation algorithm.

A blood pressure of a subject may be calculated according to equation (1):

$$PWV = \sqrt{\frac{T * E0 * e^{a*BP}}{\rho * d}}; \tag{1}$$

wherein PWV is the pulse wave velocity, T is the blood vessel wall thickness; p is the blood density; d is the interior diameter of the vessel; E0 is the arterial wall elasticity; a is a constant, and BP is the blood pressure. The coefficients in Equation (1) represent a subject's physical characteristics of the subject's cardiovascular system. The conventional methods have not been able to measure a subject's blood pressure in a reliable way using this equation because the coefficients in the equation vary from one subject to another, and vary as the subject ages. In some embodiments, the present disclosure provides a novel method of measuring the subject's blood pressure by comparing a metric of the subject's pulse wave signal with a plurality of reference metrics corresponding to a plurality of reference blood pressure calculation algorithms. Optionally, each of the reference blood pressure calculation algorithms is expressed in a form of Equation (1), and the plurality of reference blood pressure calculation algorithms are associated with a plurality of sets of different coefficients. The reference blood pressure calculation algorithm associated with a reference metric that matched closest with the metric of the subject's pulse wave signal is chosen for calculating the blood pressure of the subject under examination.

Accordingly, the method in some embodiments includes a step of establishing a database including the plurality of reference metrics corresponding to the plurality of reference blood pressure calculation algorithms, e.g., a plurality of algorithms in the form of Equation (1) with a plurality of sets of different coefficients. The database may include any appropriate number of reference algorithms corresponding to multiple health conditions in a subject, respectively.

Figure 2:
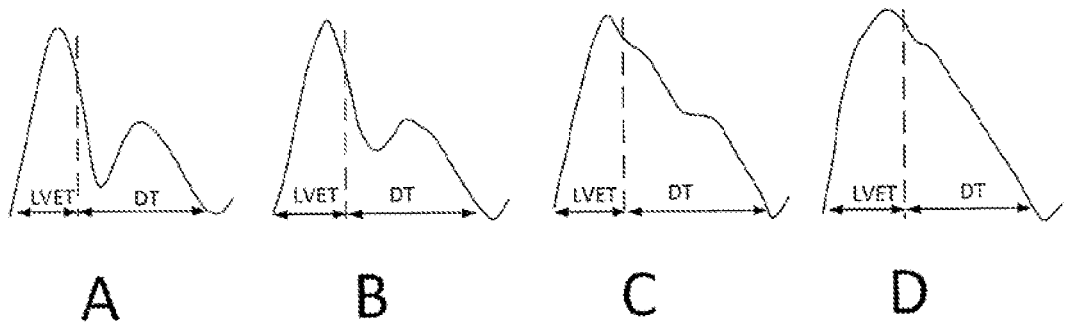
FIG. 2 illustrates pulse waves corresponding to several health conditions in some embodiments according to the present disclosure.

FIG. 2 illustrates pulse waves corresponding to several health conditions in some embodiments according to the present disclosure. Referring to FIG. 2, LVET stands for left ventricular ejection time, and DT stands for diastolic time. The pulse wave A represents a typical pulse wave from a health young adult or a subject being treated, e.g., with a thrombolytic therapy, the pulse wave A is characterized by low vascular resistance and low blood viscosity. The pulse wave B represents a typical pulse wave from a healthy adult, characterized by normal vascular resistance and normal blood viscosity. The pulse wave C represents a typical pulse wave from an elder adult, a subject having cardiovascular disease or condition, or a subject being treated with vascular contraction drugs, the pulse wave C is characterized by high vascular resistance and high blood viscosity. The pulse wave D represents a typical pulse wave from an elder adult, particularly a subject with a severe cardiovascular disease or condition, the pulse wave D is characterized by very high vascular resistance and very high blood viscosity. Each of these pulse waves corresponds to different physical coefficients, e.g., different blood vessel wall thickness; different blood density; different interior diameter of the vessel; and different arterial wall elasticity. By choosing a reference pulse wave that resembles the measured pulse wave of a subject under examination, a plurality of coefficients having the closest match with those of the subject under examination may be determined. Equation (1) is then used to calculate the blood pressure of the subject under examination.

In some embodiments, the database may include more than four representative pulse waves in FIG. 2. For example, the database may include more than 10, more than 30, more than 50, more than 100, or more than 1000 reference pulse waves. The reference pulse waves may represent individuals having different ages, gender, health conditions, disease conditions, treatment conditions, heights, weights, body mass indexes. Optionally, the database may include historical pulse wave data of the subject under examination, e.g., pulse wave data of the subject calibrated with blood pressure values obtained using other reliable methods such as sphygmomanometer, oscillometry, or invasive vascular pressure monitoring. Accordingly, the present method may be subject specific by including the subject's own calibrated data. Thus, the present method is capable of providing more accurate results as compared to conventional methods.

In some embodiments, the method further includes updating the database. For example, the database may be updated with additional reference pulse waves representing individuals in a different population, e.g., individuals with a newly discovered disease condition. Optionally, the database may be updated with the user's most recent historical pulse wave data calibrated with blood pressure values obtained using other reliable methods such as sphygmomanometer, oscillometry, or invasive vascular pressure monitoring. Optionally, the database may be updated with reference pulse waves representing individuals having a particular characteristic, e.g., diet, exercise habit, genetic traits, etc.

Referring to Equation (1), to calculate the blood pressure of a subject, it is required to determine a pulse wave velocity (PWV) of the subject. In some embodiments, the pulse wave velocity may be determined according to Equation (2):

$$PTT = \frac{D}{PWV}; \tag{2}$$

wherein PTT is pulse transit time, and D is the physical distance between two sites where two measurements are taken. Various appropriate methods may be used for calculating the pulse transit time PTT.

Figure 3:
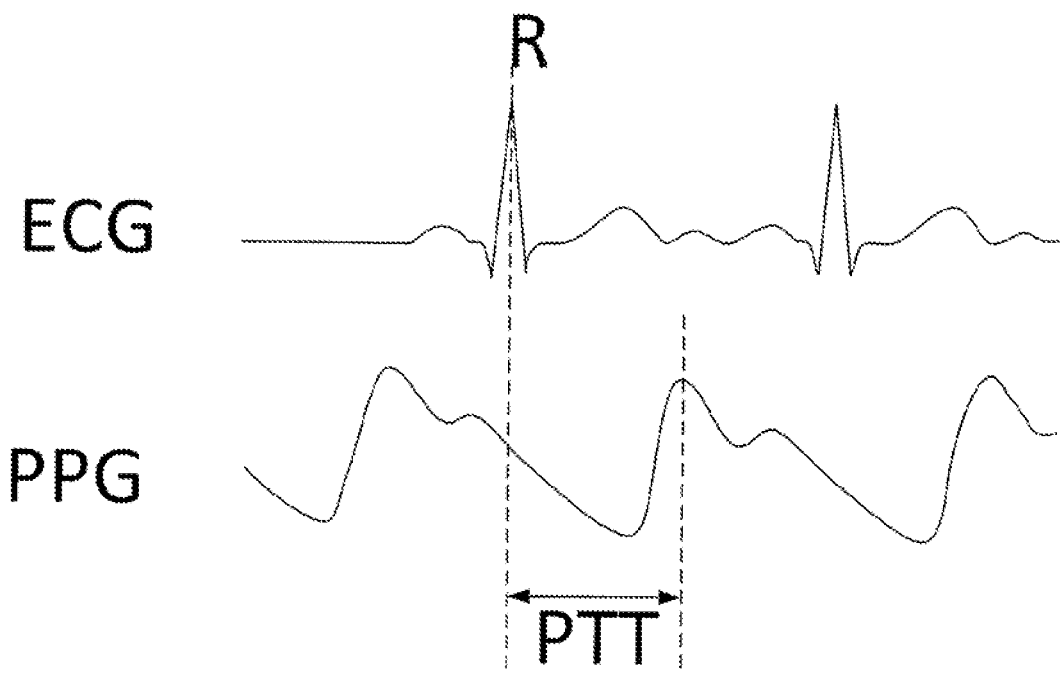
FIG. 3 is a diagram illustrating a time difference between an electrocardiography R-wave and an arterial pulse wave in some embodiments according to the present disclosure.

FIG. 3 is a diagram illustrating a time difference between an electrocardiography R-wave and an arterial pulse wave in some embodiments according to the present disclosure. Referring to FIG. 3, an arterial pulse wave originates from the heart of the subject and travels along arterial vessels to a peripheral site, at which point an arterial pulse wave is measured. The first point of the pulse wave propagation corresponds to the electrocardiography (ECG) R-wave, and the second point of the pulse wave propagation corresponds to the pulse wave measured by, e.g., photoplethysmography (PPG). Thus, in some embodiments, an electrocardiography sensor (e.g., an electrocardiography electrode) is used to measure the electrocardiography R-wave, and a photoplethysmography sensor is used to measure the pulse wave, e.g., at a peripheral arterial site. The pulse transit time (PTT) is calculated as the time difference between the electrocardiography R-wave and the arterial pulse wave as shown in FIG. 3. The first point and the second point for measuring the pulse transit time are a global maximum point in the electrocardiography R-wave and a global maximum point in the pulse wave, respectively. Optionally, other reference points (e.g., a local minimum point, a local maximum point, or a global or local maximum point of a first derivative) may be used for measuring the pulse transit time. Distance D is the distance between the heart and the peripheral arterial site.

Figure 4:
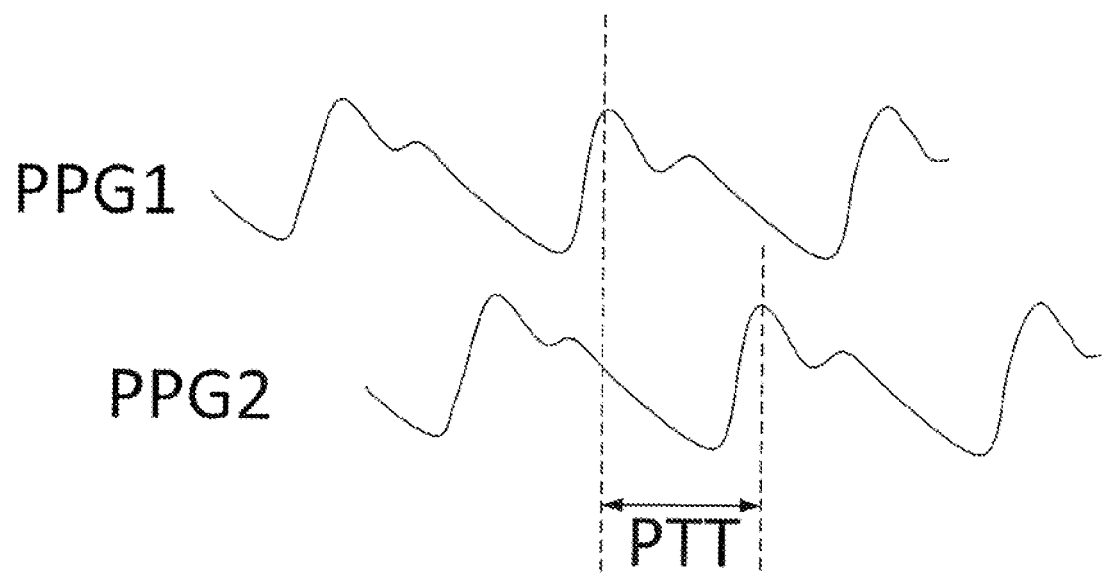
FIG. 4 is a diagram illustrating a time difference between two arterial pulse waves from two different arterial sites in some embodiments according to the present disclosure.

FIG. 4 is a diagram illustrating a time difference between two arterial pulse waves from two different arterial sites in some embodiments according to the present disclosure. Referring to FIG. 4, two pulse waves PPG1 and PPG2 from two different arterial sites are shown. In FIG. 4, the pulse waves are pulse waves measured by photoplethysmography. Other methods of measuring pulse waves may be used. Thus, in some embodiments, two different photoplethysmography sensors placed at two different arterial sites are used to measure the pulse wave. The pulse transit time is calculated as the time difference between the two arterial pulse waves. Distance D is the distance between two peripheral arterial sites. The first point and the second point for measuring the pulse transit time are two corresponding global maximum points in the two pulse waves, respectively. Optionally, other reference points (e.g., a local minimum point, a local maximum point, or a global or local maximum point of a first derivative) may be used for measuring the pulse transit time.

In some embodiments, the method includes calculating a pulse wave velocity of the subject; and determining the blood pressure of the subject using the pulse wave velocity of the subject and the selected blood pressure calculation algorithm. Optionally, the pulse wave velocity may be calculated by dividing the Distance D by the measured pulse transit time PTT, according to Equation (2). Optionally, the Distance D may be input by the user and stored in a memory. Optionally, the distance D may be pre-measured. Optionally, an estimated value may be used as the Distance D. For example, the Distance D may have a value half that of the subject's height. Optionally, the Distance D may be expressed according to the following equation (3):

$$D = 0.4861 * H + 0.6337 \text{ (cm)} \qquad (3);$$

wherein H is a subject's height.

In some embodiments, one or more relevant metric of the pulse wave signal may be used for comparison with the plurality of reference metrics. For example, the metric may be a metric in time domain of the pulse wave signal. Optionally, the metric is a metric in frequency domain of the pulse wave signal. Optionally, the metric is a metric in time-frequency domain of the pulse wave signal.

Accordingly, in some embodiments, the method further includes performing one or more of time domain analysis, frequency domain analysis, time-frequency domain analysis on the pulse wave signal. Optionally, the metric includes one or more of a metric in time domain of the pulse wave signal, a metric in frequency domain of the pulse wave signal, and a metric in time-frequency domain of the pulse wave signal.

In some embodiments, the one or more relevant metric of the pulse wave signal includes a metric in time domain of the pulse wave signal. Optionally, the metric in time domain of the pulse wave signal includes one or more of a ratio between amplitudes at two reference points in the time domain of the pulse wave signal; a ratio between $\Delta t1$ and $\Delta t2$ in the time domain of the pulse wave signal, wherein $\Delta t1$ is a first time difference between a first pair of reference points, and $\Delta t2$ is a second time difference between a second pair of reference points; a ratio between S1 and S2, wherein S1 is a first area defined by a first pair of reference points under a curve of a time domain representation of the pulse wave signal, and S2 is a second area defined by a second pair of reference points under the curve of the time domain representation of the pulse wave signal. Optionally, the metric in time domain of the pulse wave signal includes an amplitude at a reference point, a time difference between a pair of reference points, and an area defined by a pair of reference points under a curve of a time domain representation of the pulse wave signal. Optionally, the reference point may be one of a global maximum point, a global minimum point, a local maximum point, a local minimum point, a global maximum point of a first derivative, a global minimum point of a first derivative, a local maximum point of a first derivative, and a local minimum point of a first derivative, in time domain of a pulse wave signal.

Figure 5:
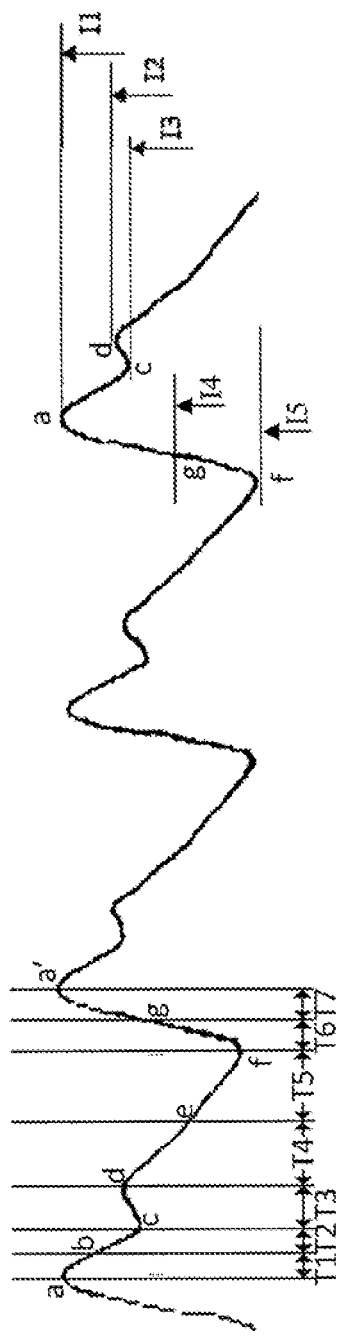
FIG. 5 is an exemplary time domain signal in some embodiments according to the present disclosure.

FIG. 5 is an exemplary time domain signal in some embodiments according to the present disclosure. Referring to the FIG. 5, the pulse wave includes several reference points in the time domain: a, b, c, d, e, f, g, h, and a'. Among these, reference points a and a' are global maximum points, reference point f is a global minimum point, reference point c is a local minimum point, reference point d is a local maximum point, reference points b, e, and g are local maximum points of absolute vale of a first derivative of the pulse wave. An amplitude corresponding to reference point a is I1, an amplitude corresponding to reference point d is I2, an amplitude corresponding to reference point c is I3, an amplitude corresponding to reference point g is I4, and an amplitude corresponding to reference point f is I5. A time difference between reference points a and b in the time domain is T1, a time difference between reference points b and c in the time domain is indicated as T1, a time difference between reference points c and d in the time domain is indicated as T3, a time difference between reference points d and e in the time domain is indicated as T4, a time difference between reference points e and f in the time domain is indicated as T5, a time difference between reference points f and g in the time domain is indicated as T6, and a time difference between reference points g and h in the time domain is indicated as T7. In one example, a relevant metric of the pulse wave signal is a ratio between any pair of I1, I2, I3, I4, and I5. In another example, a relevant metric of the pulse wave signal is a ratio between any pair of T1, T2, T3, T4, T5, T6, and T7.

Figure 6:
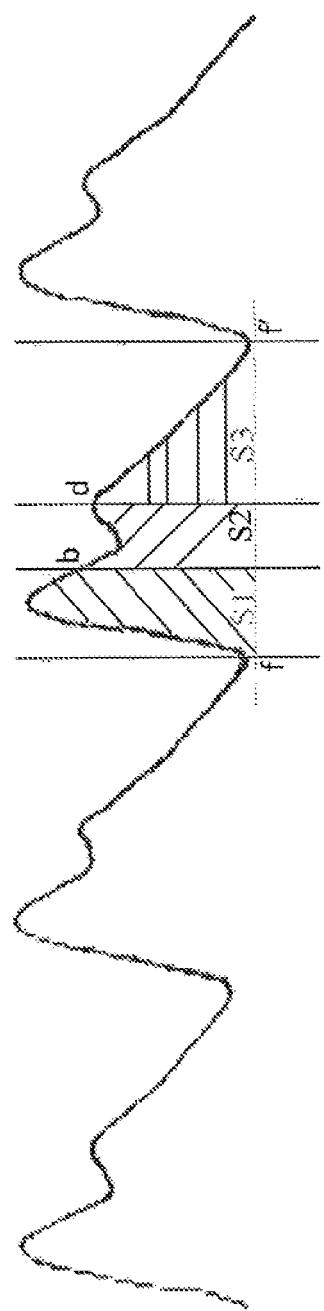
FIG. 6 is an exemplary time domain signal in some embodiments according to the present disclosure.

FIG. 6 is an exemplary time domain signal in some embodiments according to the present disclosure. Referring to FIG. 6, reference point b is a local maximum point of absolute value of a first derivative of the pulse wave, reference point d is a local maximum point, reference points f and f' are global minimum points. S1 is a first area defined by the reference point f and the reference point b under a curve of a time domain representation of the pulse wave signal, S2 is a second area defined by the reference point b and the reference point d under the curve of the time domain representation of the pulse wave signal, and S3 is a third area defined by the reference point d and the reference point f' under the curve of the time domain representation of the pulse wave signal. In one example, a relevant metric of the pulse wave signal is a ratio between any pair of S1, S2, and S3.

In some embodiments, the one or more relevant metric of the pulse wave signal includes a metric in frequency domain of the pulse wave signal. Optionally, the metric in frequency domain of the pulse wave signal includes a frequency with a highest energy level. Optionally, the metric in frequency domain of the pulse wave signal includes a plurality of frequencies with highest energy levels. By comparing a frequency with a highest energy level or a plurality of frequencies with highest energy levels with that or those in frequency domains of a plurality of reference pulse waves, a closest match among the plurality of reference pulse waves may be chosen, and a blood pressure calculation algorithm corresponding to the chosen reference pulse wave may be used for calculating the blood pressure of the subject under examination.

Additional frequency domain metrics that may be used in the present method include, but are not limited to, a fundamental frequency of a signal, a frequency of one or more integer harmonics of the signal, a phase value of the fundamental frequency, a phase value at the frequency of the one or more integer harmonics of the signal, a frequency change in the fundamental frequency, a frequency change in one or more frequencies of the one or more integer harmonics, a phase change in the fundamental frequency, a phase change in one or more frequencies of the one or more integer harmonics, a power amplitude at the fundamental frequency of the signal, a power amplitude at each frequency of the one or more integer harmonics of the signal, a frequency dispersion about the fundamental frequency of the signal, and a frequency dispersion about the frequency of the one or more integer harmonics of the signal.

Figure 7:
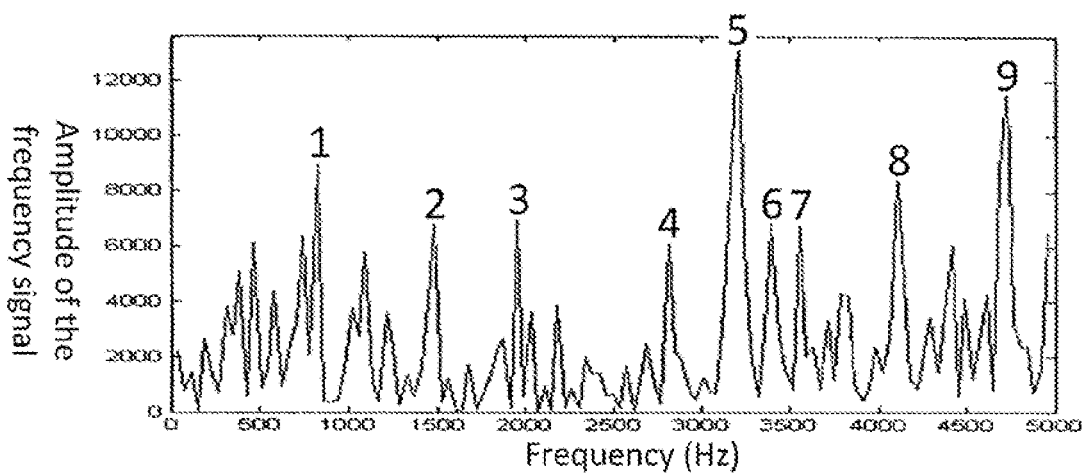
FIG. 7 is an exemplary frequency domain signal in some embodiments according to the present disclosure.

FIG. 7 is an exemplary frequency domain signal in some embodiments according to the present disclosure. Referring to FIG. 7, the pulse wave includes several reference points in the frequency domain: 1, 2, 3, 4, 5, 6, 7, 8, and 9. These reference points represent nine global or local maximum points in the frequency domain. In some examples, a relevant metric of the pulse wave signal is the frequency with a highest energy level at reference point 5 (e.g., a global maximum point). In some examples, a relevant metric of the pulse wave signal is the frequencies with highest energy levels at reference points 1, 5, and 9. In some examples, a relevant metric of the pulse wave signal is the frequencies with highest energy levels at reference points 1, 2, 3, 5, 8, and 9. In some examples, a relevant metric of the pulse wave signal is the frequencies with highest energy levels at reference points 1, 2, 3, 4, 5, 6, 7, 8, and 9 (e.g., global and local maximum points).

In some embodiments, the one or more relevant metric of the pulse wave signal includes a metric in time-frequency domain of the pulse wave signal. Optionally, the metric in time-frequency domain of the pulse wave signal includes a correlation between a frequency domain metric and a time domain metric. By comparing the correlation with a plurality of reference correlations in time-frequency domain of a plurality of reference pulse waves, a closest match among the plurality of reference pulse waves may be chosen, and a blood pressure calculation algorithm corresponding to the chosen reference pulse wave may be used for calculating the blood pressure of the subject under examination.

Figure 8:
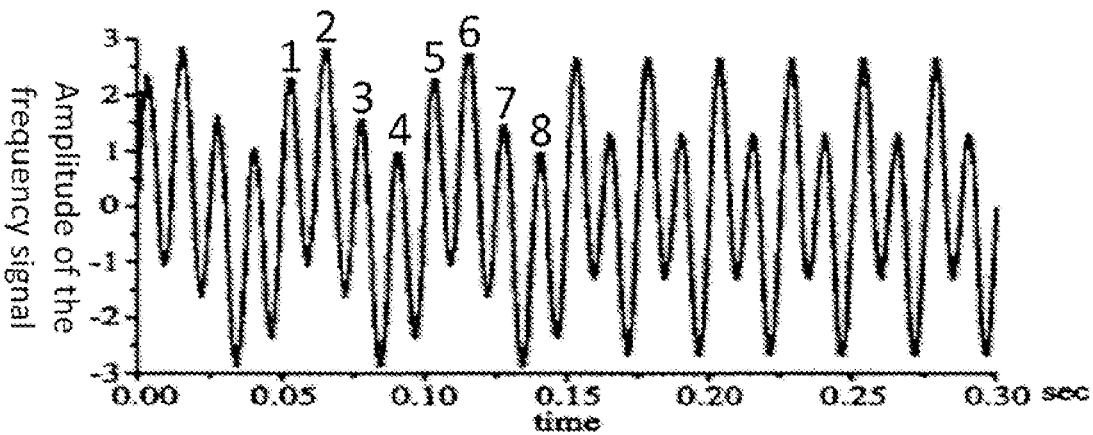
FIG. 8 is an exemplary time-frequency domain signal in some embodiments according to the present disclosure.

FIG. 8 is an exemplary time-frequency domain signal in some embodiments according to the present disclosure. Referring to FIG. 8, the pulse wave includes several reference points 1, 2, 3, 4, 5, 6, 7, and 8, corresponding to eight global or local maximum points in the time-frequency domain. In some examples, a relevant metric of the pulse wave signal is a value at the reference points 2 and 6 (e.g., global maximum points). In some examples, a relevant metric of the pulse wave signal is values at reference points 1, 2, 5, and 6. In some examples, a relevant metric of the pulse wave signal is values at reference points 1, 2, 3, 4, 5, 6, 7, and 8 (e.g., global and local maximum points).

In some embodiments, frequency domain signals may be generated by a Fourier transformation of time domain signals. In some embodiments, time-frequency domain signals may be generated by transforming time domain signals and/or frequency domain signals using one or more of a short-time Fourier transformation, a continuous wavelet transformation, a Hilbert-Huang transformation, and a Wigner distribution function.

Accordingly, the database may further include a plurality of reference metrics corresponding to the plurality of reference pulse wave signals stored in the database. In some embodiments, the plurality of reference metrics includes one or more of a reference metric in time domain of a reference pulse wave signal, a reference metric in frequency domain of a reference pulse wave signal, and a reference metric in time-frequency domain of a reference pulse wave signal. In some embodiments, the method further includes performing one or more of time domain analysis, frequency domain analysis, time-frequency domain analysis on the plurality of reference pulse wave signals.

Optionally, the reference metric in time domain of a reference pulse wave signal includes one or more of a ratio between amplitudes at two reference points in the time domain of the reference pulse wave signal; a ratio between $\Delta t1$ and $\Delta t2$ in the time domain of the reference pulse wave signal, wherein $\Delta t1$ is a first time difference between a first pair of reference points, and $\Delta t2$ is a second time difference between a second pair of reference points; a ratio between S and S2, wherein S1 is a first area defined by a first pair of reference points under a curve of a time domain representation of the reference pulse wave signal, and S2 is a second area defined by a second pair of reference points under the curve of the time domain representation of the reference pulse wave signal. Optionally, the reference metric in time domain of the reference pulse wave signal includes an amplitude at a reference point, a time difference between a pair of reference points, and an area defined by a pair of reference points under a curve of a time domain representation of the reference pulse wave signal. Optionally, the reference point may be one of a global maximum point, a global minimum point, a local maximum point, a local minimum point, a global maximum point of a first derivative, a global minimum point of a first derivative, a local maximum point of a first derivative, and a local minimum point of a first derivative, in time domain of a reference pulse wave signal. Optionally, the reference metric in frequency domain of the reference pulse wave signal includes a frequency with a highest energy level. Optionally, the reference metric in frequency domain of the reference pulse wave signal includes a plurality of frequencies with highest energy levels. Optionally, the reference metric in time-frequency domain of the reference pulse wave signal includes a correlation between a frequency domain metric and a time domain metric.

In some embodiments, the plurality of reference pulse wave signals in the database are a plurality of composite pulse wave signals. For example, a composite pulse wave signal may be a model composite pulse wave signal representative of a group of subjects having certain common characteristics, e.g., age, gender, health condition, disease condition, treatment condition, height, weight, body mass index. Each metric in a model composite pulse wave signal is representative of the metric in the group of subjects having common characteristics. For example, a value of each metric may be an average or medium value of metrics of pulse wave signals collected from the group of subjects having common characteristics. In some examples, the database may include one or more of a first composite pulse wave signal representing health young adults or subjects undergoing treatment, a second composite pulse wave signal representing healthy adults, a third composite pulse wave signal representing elder adults or subjects undergoing vascular contraction treatment, and a fourth composite pulse wave signal representing elder adults with a severe cardiovascular disease or condition. In some embodiments, the database includes additional composite pulse wave signals, each representing a population or sub-population.

In some embodiments, each metric in a composite pulse wave signal may have a range of values or an average or median value from the group of subjects represented by the composite pulse wave signal. A closest match between a pulse wave signal and a plurality of reference pulse wave signals may be found if each metric or a majority of metrics of the pulse wave signal measured from a subject is within a range defined by a reference pulse wave signal.

In some embodiments, the present disclosure provides a predictive modeling method for assigning a subject's blood pressure based on one or more measured relevant metric of pulse wave signal, i.e., the blood pressure calculation algorithm is derived from a prediction model established using a plurality of reference metrics of a plurality of reference pulse wave signals. Any appropriate predictive modeling method may be used for assigning the blood pressure. Examples of appropriate predictive modeling methods include, but are not limited to, ordinary least squares regression, linear least squares regression, mean squared error, a generalized linear model, logistic regression model, classification model, regression tree model, multivariate adaptive regression spline model, etc.

For example, in some embodiments, the ordinary least squares regression method is used as the prediction model for assigning a subject's blood pressure. In one example, systolic blood pressure (SBP) may be determined by $$SBP = X*A \tag{4}$$

wherein $$X = \begin{bmatrix} x_1 \\ x_2 \\ \vdots \\ x_n \end{bmatrix};$$

$x_1, x_2, \ldots, x_n$ are relevant metrics of pulse wave signal as discussed above; $A[a_1, a_2, \ldots, a_n]$, which is a matrix of regression coefficients.

In another example, diastolic blood pressure (DBP), and may be determined by $$DBP = X*B \tag{5}$$

wherein $$X = \begin{bmatrix} x_1 \\ x_2 \\ \vdots \\ x_n \end{bmatrix};$$

$x_1, x_2, \ldots, x_n$ are relevant metrics of pulse wave signal as discussed above; $B=[b_1, b_2, \ldots, b_n]$, which is a matrix of regression coefficients.

In some embodiments, A and B may be determined by the ordinary least squares regression method. For this modeling method, the following equation applies:

$$Y_i = \beta_0 + \beta_1 X_1 + \ldots + \beta_k X_{ki} (i=1 \ldots n) \tag{6}$$

wherein $Y_i$ is the blood pressure (SBP or DBP), which is a function of predictor variables $X_{1i}, X_{2i}, \ldots, X_{ki}$; each of $\beta_1, \beta_2, \ldots, \beta_k$ is a regression coefficient for a corresponding predictor variable. The predictor variables $X_{1i}, X_{2i}, \ldots, X_{ki}$ correspond to X in equation (4) or (5). The regression coefficients $\beta_1, \beta_2, \ldots, \beta_k$ correspond to A or B in equation (4) or (5). In the ordinary least squares regression method, the coefficients are estimated by minimizing the sum of squared errors (SSE).

In some embodiments, the ordinary least squares regression model and regression coefficients thereof are established by a plurality of pulse wave data and corresponding blood pressure values obtained using reference methods such as sphygmomanometer, oscillometry, or invasive vascular pressure monitoring. The regression model may be established using a large number of reference data.

In some embodiments, a plurality of ordinary least squares regression models and regression coefficients thereof may be established for a plurality of groups of sub-populations, respectively. Each of the plurality of groups of sub-populations may have one or more common characteristic, e.g., age, gender, health condition, disease condition, treatment condition, height, weight, and body mass index. When applying the method to determine a subject's blood pressure, the subject may be first classified by the one or more common characteristics. The method further includes selecting the regression model from a plurality of reference prediction models established for a plurality of subpopulations, respectively. A regression model that best fits the subject is then chosen based on the classification, and is used for calculating the subject's blood pressure.

Accordingly, in another aspect, the present disclosure provides a method of diagnosing a disease or a condition in a subject. In some embodiments, the method includes measuring a pulse wave signal of the subject; comparing a metric of the pulse wave signal with a plurality of reference metrics corresponding to a plurality of disease or health conditions; selecting a matched reference pulse wave signal having a closet resemblance to the pulse wave signal of the subject based on a result of the comparing; and assigning a disease or health condition corresponding to the matched reference pulse wave signal as a diagnosed disease or health condition for the subject. The measuring step, the comparing step, and the selecting step may be performed according to methods described above.

In another aspect, the present disclosure further provides a method of monitoring a disease or health condition of a subject. For example, the method may be a method of continuously monitoring a disease or health condition of a subject over a period of time. In some embodiments, the method includes continuously or periodically measuring a pulse wave signal of the subject; comparing a metric of the pulse wave signal with a plurality of reference metrics corresponding to a plurality of disease or health conditions; selecting a matched reference pulse wave signal having a closet resemblance to the pulse wave signal of the subject based on a result of the comparing; and transmitting a signal to a receiver when the matched reference pulse wave signal corresponding to an abnormal disease condition. Optionally, the receiver is the user. Optionally, the receiver is a caretaker of the user. Optionally, the receiver is a healthcare professional. Optionally, the receiver is a hospital or a clinic. Optionally, the abnormal disease condition is a stroke.

In another aspect, the present disclosure provides a method of treating a subject. In some embodiments, the method of treating a subject includes continuously or periodically measuring a pulse wave signal of the subject; comparing a metric of the pulse wave signal with a plurality of reference metrics corresponding to a plurality of disease or health conditions; selecting a matched reference pulse wave signal having a closet resemblance to the pulse wave signal of the subject based on a result of the comparing; and administering a therapy to the subject when the matched reference pulse wave signal corresponding to an abnormal disease condition. Optionally, the abnormal disease condition is a stroke. Optionally, the treatment is a thrombolytic therapy.

In some embodiments, the disease or condition is one or more of acute coronary syndrome, sudden cardiac death, arrhythmia, stroke, myocardial infarction, cardiac Ischemia, endothelial dysfunction, coronary artery disease, coronary artery occlusion, arterial stiffness, autonomic nervous system function, angina pectoris, and atherosclerosis.

Optionally, the subject is a human. Optionally, the subject is a mammal. Optionally, the subject is a pet (e.g., a dog, a cat).

In another aspect, the present disclosure provides an apparatus for determining a blood pressure of a subject. In some embodiments, the apparatus includes a sensor assembly configured to measure a pulse wave signal of the subject; and a signal processor configured to generate a metric of the pulse wave signal; to select a blood pressure calculation algorithm; and to determine the blood pressure of the subject using the blood pressure calculation algorithm. Optionally, the signal processor is configured to compare, directly or indirectly, a metric of the pulse wave signal with a plurality of reference metrics of a plurality of reference pulse wave signals; to obtain a blood pressure calculation algorithm; and to determine the blood pressure of the subject using the blood pressure calculation algorithm.

Optionally, the apparatus is a cuff-less apparatus. Optionally, the apparatus is a wearable apparatus. Optionally, the apparatus is a continuously wearable apparatus. Optionally, the apparatus is a portable blood pressure measuring apparatus.

In one example, the signal processor is configured to calculate a pulse wave velocity of the subject based on the pulse wave signal measured by the sensor assembly; compare the metric of the pulse wave signal with a plurality of reference metrics of a plurality of reference pulse wave signals; select the blood pressure calculation algorithm from a plurality of reference blood pressure calculation algorithms associated with the plurality of reference pulse wave signals, respectively, based on a result of the comparing; and determine the blood pressure of the subject using the pulse wave velocity of the subject and the selected blood pressure calculation algorithm.

In another example, the blood pressure calculation algorithm is derived from a prediction model established using a plurality of reference metrics of a plurality of reference pulse wave signals. Optionally, the signal processor is configured to select the prediction model from a plurality of reference prediction models established for a plurality of subpopulations, respectively.

Figure 9:
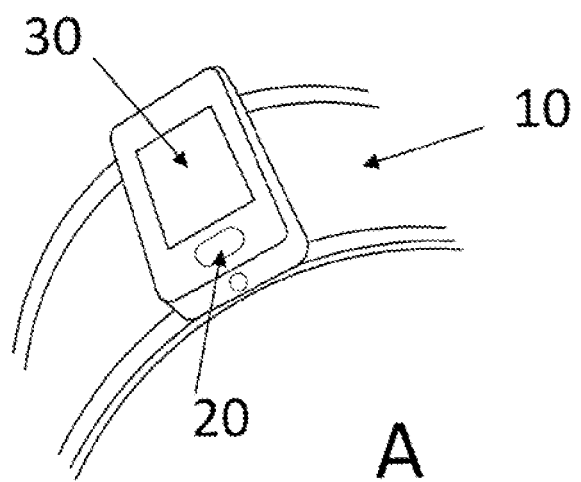
FIG. 9 is a diagram illustrating a wearable apparatus in some embodiments according to the present disclosure.
Figure 9:
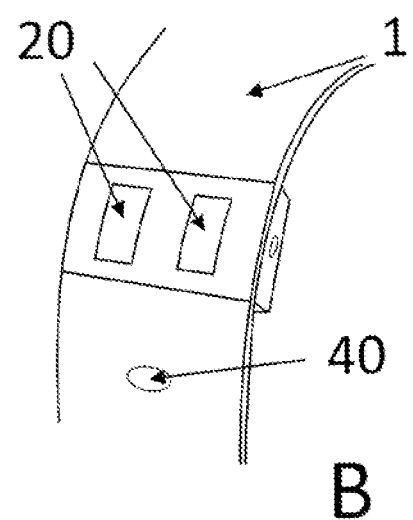

FIG. 9 is a diagram illustrating a wearable apparatus in some embodiments according to the present disclosure. Referring to FIG. 9, the wearable apparatus in the embodiment includes a front side A and a back side B. The front side A of the wearable apparatus includes a belt 10, a display 30, and an electrocardiography electrode 20. The back side B of the wearable apparatus includes a photoplethysmography sensor 40, and two electrocardiography electrodes 20.

In some embodiments, the sensor assembly includes at least one pulse wave sensor. Optionally, the pulse wave sensor is a photoplethysmography sensor. Examples of appropriate pulse wave sensors further include, but are not limited to, an ultrasound transducer (e.g., a piezoelectric ultrasound transducer), laser Doppler or other an optical blood flow sensor (e.g., a laser Doppler optical blood flow sensor), and a pressure or force sensor.

In some embodiments, the sensor assembly further includes at least a sensor for measuring electrocardiography R-wave. Optionally, the sensor for measuring electrocardiography R-wave includes one or more electrocardiography electrodes. Optionally, the sensor for measuring electrocardiography R-wave includes a plurality of electrocardiography electrodes, e.g., 2, 3, or more electrodes.

In some embodiments, the sensor assembly includes at least one pulse wave sensor and at least one sensor for measuring electrocardiography R-wave (e.g., an electrocardiography electrode and a photoplethysmography sensor). In some embodiments, the sensor assembly includes at least two pulse wave sensors (e.g., two photoplethysmography sensors for measuring pulse waves at two arterial sites). Optionally, all sensors are integrated into the apparatus. Optionally, at least one sensor may be separate from the apparatus's main body and is in remote communication with (e.g., via wireless connection) the processor in the apparatus's main body. Optionally, the main body of the apparatus may be worn on one location of a subject (e.g., the wrist of the subject), and another sensor may be placed on an arterial site away from the main body (e.g., on the subject's leg).

Figure 10:
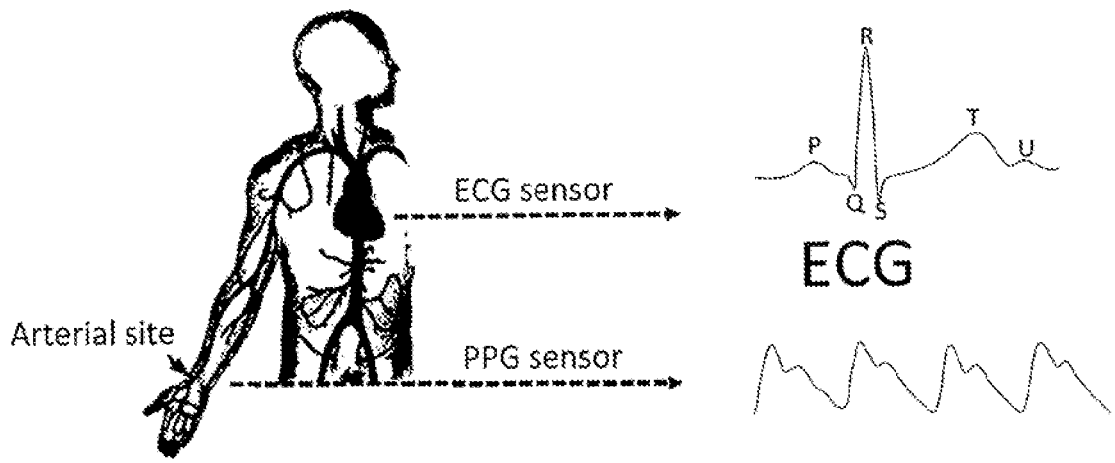
FIG. 10 illustrates a subject wearing a wearable apparatus in some embodiments according to the present disclosure.

FIG. 10 illustrates a subject wearing a wearable apparatus in some embodiments according to the present disclosure. Referring to FIG. 10, the sensor assembly in the embodiment includes an electrocardiography sensor (ECG sensor) for measuring an electrocardiography R-wave and a photoplethysmography sensor (PPG sensor) for measuring a pulse wave.

Figure 11:
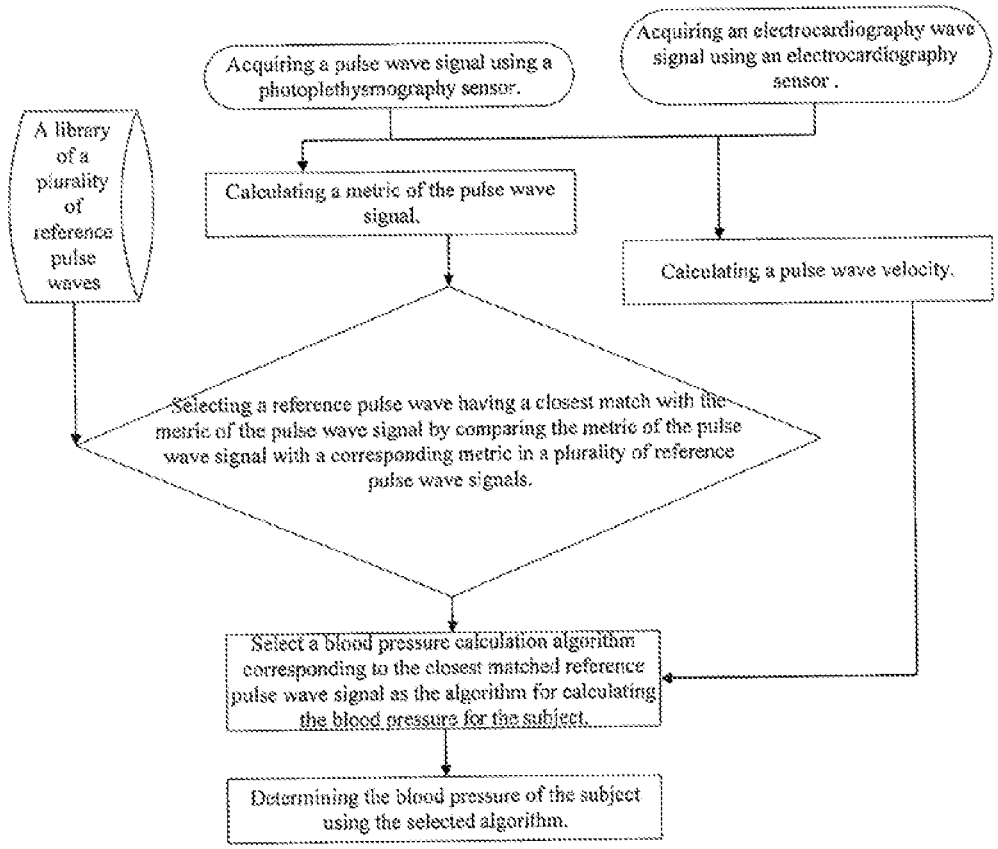
FIG. 11 is a diagram illustrating a process of measuring a blood pressure of a subject using an apparatus in some embodiments according to the present disclosure.

FIG. 11 is a diagram illustrating a process of measuring a blood pressure of a subject using an apparatus in some embodiments according to the present disclosure. Referring to FIG. 11, the process in the embodiment includes acquiring a pulse wave signal using a photoplethysmography sensor and acquiring an electrocardiography wave signal using an electrocardiography sensor. Once the pulse wave signal is acquired, one or more metric of the acquired pulse wave signal is calculated. The calculated metric is compared against corresponding metrics of a plurality of reference pulse waves stored in a database. Based on the result of the comparison, a reference pulse wave may be selected having a closest match with the metric of the acquired pulse wave signal. As shown in FIG. 11, a blood pressure calculation algorithm corresponding to the closest matched reference pulse wave signal is selected as the algorithm for calculating the blood pressure for the subject. Moreover, a pulse wave velocity can be calculated by using the acquired pulse wave signal and the acquired electrocardiography wave. Accordingly, the blood pressure of the subject may be accurately determined using the selected algorithm and the calculated pulse wave velocity.

Figure 12:
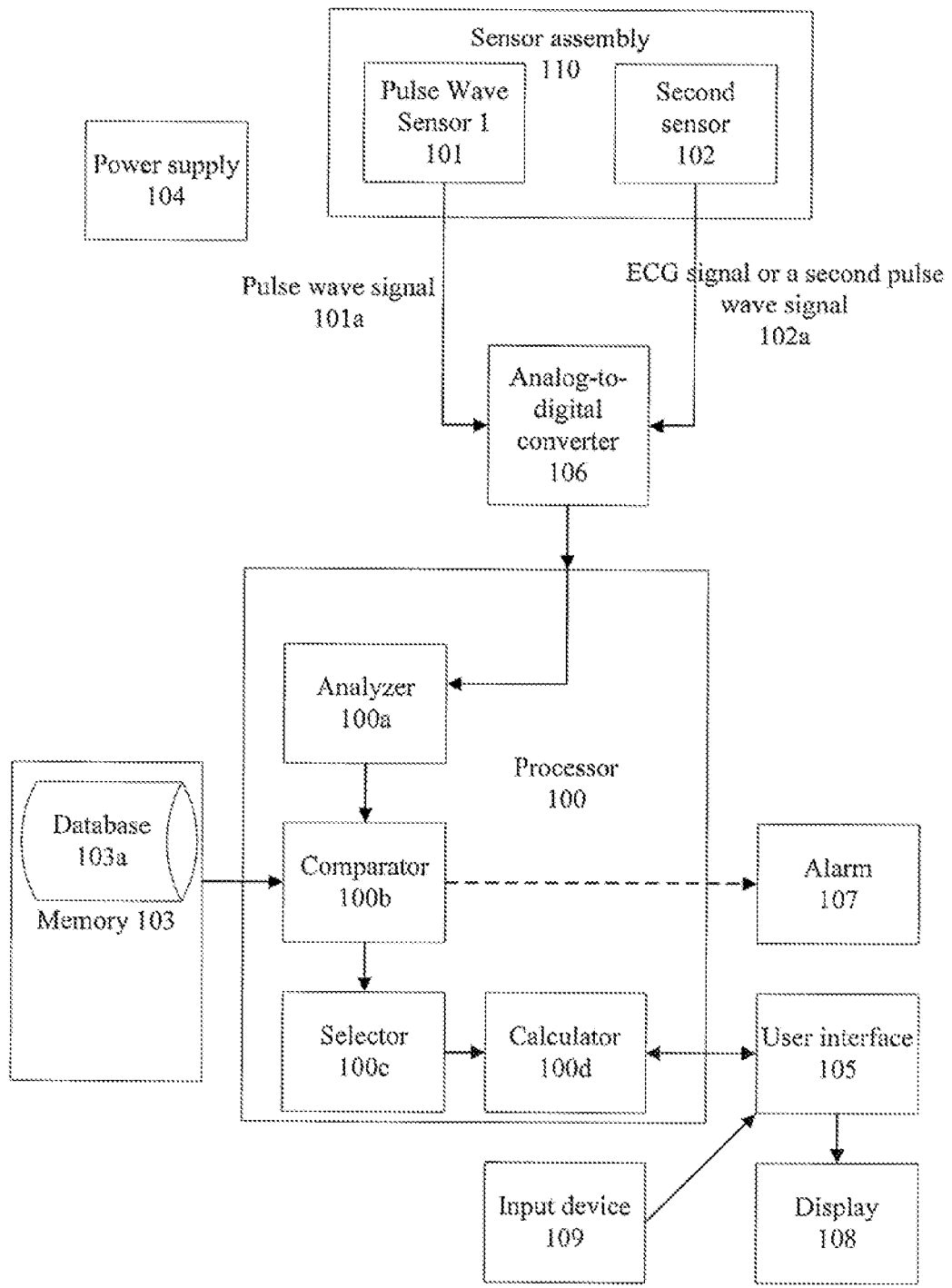
FIG. 12 is a diagram illustrating the structure of an apparatus in some embodiments according to the present disclosure.

FIG. 12 is a diagram illustrating the structure of an apparatus in some embodiments according to the present disclosure. Referring to FIG. 12, the apparatus in the embodiment includes a processor 100 and a sensor assembly 110. The sensor assembly 110 includes a pulse wave sensor 101 for measuring a pulse wave signal 101a of a subject and a second sensor 102 for measuring an electrocardiography (ECG) signal 102a or a second pulse wave signal 102a. The second sensor 102 may be a pulse wave sensor or an electrocardiography wave sensor, as discussed above. Optionally, the apparatus further includes a power supply 104 for providing power to the apparatus.

In some embodiments, the apparatus further includes a data converter such as an analog-to-digital converter 106 in FIG. 12 for converting the pulse wave signal measured by the sensor assembly into digital data, and transmitting the digital data to the processor 100 for analysis.

In some embodiments, the apparatus further includes a user interface 105 for displaying information on a display 108 and for the user to input data to the apparatus through an input device 109. The user may input data related to a subject's height, weight, and other physical parameters and genetic traits, and historical pulse wave data of the subject. In some embodiments, the apparatus further includes an alarm 107 for transmitting a signal to a receiver when an abnormal disease condition is detected in the subject.

In some embodiments, the apparatus further includes a memory 103 for storing the digital data, the plurality of reference metrics, the plurality of reference blood pressure calculation algorithms, and the plurality of reference pulse wave signals. Optionally, the memory 103 includes a database 103a. Optionally, the database 103a contains data related to the plurality of reference metrics, the plurality of reference blood pressure calculation algorithms, and the plurality of reference pulse wave signals. Optionally, the plurality of reference metrics include one or more of a metric in time domain of a reference pulse wave signal, a metric in frequency domain of a reference pulse wave signal, and a metric in time-frequency domain of a reference pulse wave signal.

Referring to FIG. 12, in some embodiments, the processor 100 includes an analyzer 100a for performing one or more of time domain analysis, frequency domain analysis, time-frequency domain analysis on the pulse wave signal of the subject. Optionally, the metric includes one or more of a metric in time domain of the pulse wave signal, a metric in frequency domain of the pulse wave signal, and a metric in time-frequency domain of the pulse wave signal. Optionally, the analyzer 100a is configured to perform one or more of time domain analysis, frequency domain analysis, time-frequency domain analysis on the plurality of reference pulse wave signals.

In some embodiments, the processor 100 further includes a comparator 100b for comparing the metric of the pulse wave signal with a plurality of reference metrics of a plurality of reference pulse wave signals. The comparator 100b is in communication with the memory 103.

In some embodiments, the processor 100 further includes a selector 100c for selecting a blood pressure calculation algorithm from the plurality of reference blood pressure calculation algorithms associated with the plurality of reference pulse wave signals, respectively, based on the result of the comparing performed by the comparator 100h. For example, the reference blood pressure calculation algorithm associated with the closest matched reference pulse wave signal may be selected by the selector 100c as the blood pressure calculation algorithm.

In some embodiments, the processor 100 further includes a calculator 100d for calculating the blood pressure of the subject using the selected blood pressure calculation algorithm. Optionally, the calculator 100d is configured to calculate a pulse wave velocity of the subject; and calculate the blood pressure of the subject using the pulse wave velocity of the subject and the selected blood pressure calculation algorithm.

Optionally, the sensor assembly 110 includes an electrocardiography sensor configured to measure an electrocardiography R-wave and a pulse wave sensor configured to measure an arterial pulse wave; the calculator 100d is configured to calculate a time difference between the electrocardiography R-wave and the arterial pulse wave as a pulse transit time.

Optionally, the sensor assembly 110 includes at least two pulse wave sensors configured to measure arterial pulse waves at least two arterial sites; the calculator 100d is configured to calculate a time difference between the two arterial pulse waves as a pulse transit time.

In some embodiments, the metric in time domain of the pulse wave signal includes one or more of a ratio between amplitudes at two reference points in the time domain of the pulse wave signal; a ratio between $\Delta t1$ and $\Delta t2$ in the time domain of the pulse wave signal, wherein $\Delta t1$ is a first time duration between a first pair of reference points, and $\Delta t2$ is a second time duration between a second pair of reference points; a ratio between S1 and S2, wherein S1 is a first area defined by a first pair of reference points under a curve of a time domain representation of the pulse wave signal, and S2 is a second area defined by a second pair of reference points under the curve of the time domain representation of the pulse wave signal. Optionally, the reference point may be one of a global maximum point, a global minimum point, a local maximum point, a local minimum point, a global maximum point of a first derivative, a global minimum point of a first derivative, a local maximum point of a first derivative, and a local minimum point of a first derivative, in the time domain of the pulse wave signal. Optionally, the reference point may be one of a global maximum point, a global minimum point, a local maximum point, a local minimum point, a global maximum point of a first derivative, a global minimum point of a first derivative, a local maximum point of a first derivative, and a local minimum point of a first derivative, in time domain of a pulse wave signal.

In some embodiments, the metric in frequency domain of the pulse wave signal includes a plurality of frequencies with highest energy levels.

In some embodiments, the metric in time-frequency domain of the pulse wave signal includes a correlation between a frequency domain metric and a time domain metric.

In some embodiments, the apparatus further includes a wireless transceiver for receiving or transmitting information from or to a remote site. For example, the apparatus may receive real-time database updates through the wireless transceiver.

In some embodiments, the apparatus further includes a GPS for measuring the subject's location. When an abnormal disease condition is detected in the subject, the alarm may send the location information to a healthcare professional, for example, an ambulance may be dispatched in response to the alarm to the subject's location.

In some embodiments, the present disclosure provides an apparatus including a processor, a sensor assembly having at least a pulse wave sensor for measuring a pulse wave signal of a subject, and a memory having a database. Optionally, the database contains at least one prediction model and at least one blood pressure calculation algorithm derived from the at least one prediction model. Optionally, the database contains a plurality of prediction models and a plurality of blood pressure calculation algorithms derived from the plurality of prediction models, respectively. Optionally, the database contains a plurality of prediction models established for a plurality of subpopulations, respectively, and a plurality of blood pressure calculation algorithms derived from the plurality of prediction models, respectively. For example, individuals in the plurality of subpopulations may be classified according to one or more of common characteristic, e.g., age, gender, health condition, disease condition, treatment condition, height, weight, body mass index. Optionally, the database further includes a plurality of reference pulse wave signals and a plurality of reference metrics corresponding to the plurality of reference pulse wave signals. Optionally, the plurality of reference metrics include one or more of a metric in time domain of a reference pulse wave signal, a metric in frequency domain of a reference pulse wave signal, and a metric in time-frequency domain of a reference pulse wave signal. Optionally, the signal processor is configured to generate a metric of the pulse wave signal; to select a blood pressure calculation algorithm; and to determine the blood pressure of the subject using the blood pressure calculation algorithm. Optionally, the blood pressure calculation algorithm is derived from a prediction model established using a plurality of reference metrics of a plurality of reference pulse wave signals. Optionally, the signal processor is configured to select the prediction model from a plurality of reference prediction models established for a plurality of subpopulations, respectively. Optionally, the database may be periodically updated with additional predictive models and additional blood pressure calculation algorithms.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated.

It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. An apparatus for determining a blood pressure of a subject, comprising:
    a sensor assembly configured to measure a pulse wave signal of the subject; and
    a signal processor configured to generate a metric of the pulse wave signal based on the pulse wave signal, to select a blood pressure calculation algorithm based on the metric of the pulse wave signal, to determine the blood pressure of the subject using the blood pressure calculation algorithm, and to perform frequency domain analysis, and time-frequency domain analysis on the pulse wave signal of the subject;
    wherein the signal processor is configured to perform time domain analysis on the pulse wave signal of the subject;
    the metric comprises a metric in time domain of the pulse wave signal, a metric in frequency domain of the pulse wave signal, and a metric in time-frequency domain of the pulse wave signal;
    the metric in time domain of the pulse wave signal comprises at least one of (1) a ratio between amplitudes at two reference points in the time domain of the pulse wave signal; (2) a ratio between $\Delta t1$ and $\Delta t2$ in the time domain of the pulse wave signal, wherein $\Delta t1$ is a first time difference between a first pair of reference points, and $\Delta t2$ is a second time difference between a second pair of reference points; or (3) a ratio between S1 and S2, wherein S1 is a first area defined by a first pair of reference points under a curve of a time domain representation of the pulse wave signal, and S2 is a second area defined by a second pair of reference points under the curve of the time domain representation of the pulse wave signal.

2. The apparatus of claim 1, wherein the metric in time domain of the pulse wave signal comprises all of (1) the ratio between amplitudes at two reference points in the time domain of the pulse wave signal; (2) the ratio between $\Delta t1$ and $\Delta t2$ in the time domain of the pulse wave signal; and (3) the ratio between S1 and S2.

3. The apparatus of claim 1, wherein
    the metric in frequency domain of the pulse wave signal comprises a plurality of frequencies with highest energy levels.

4. An apparatus for determining a blood pressure of a subject, comprising:
  a sensor assembly configured to measure a pulse wave signal of the subject; and
  a signal processor configured to generate a metric of the pulse wave signal based on the pulse wave signal, to select a blood pressure calculation algorithm based on the metric of the pulse wave signal, and to determine the blood pressure of the subject using the blood pressure calculation algorithm;
  wherein the signal processor is configured to perform time domain analysis on the pulse wave signal of the subject,
  the metric comprises a metric in time domain of the pulse wave signal;
  the metric in time domain of the pulse wave signal comprises at least one of (1) a ratio between amplitudes at two reference points in the time domain of the pulse wave signal; (2) a ratio between Δt1 and Δt2 in the time domain of the pulse wave signal, wherein Δt1 is a first time difference between a first pair of reference points, and Δt2 is a second time difference between a second pair of reference points; or (3) a ratio between S1 and S2, wherein S1 is a first area defined by a first pair of reference points under a curve of a time domain representation of the pulse wave signal, and S2 is a second area defined by a second pair of reference points under the curve of the time domain representation of the pulse wave signal;
  wherein the signal processor is further configured to perform time-frequency domain analysis on the pulse wave signal of the subject;
  the metric comprises a metric in time-frequency domain of the pulse wave signal; and
  the metric in time-frequency domain of the pulse wave signal comprises a correlation between a frequency domain metric and a time domain metric.

5. The apparatus of claim 1, wherein the signal processor is configured to calculate a pulse wave velocity of the subject based on the pulse wave signal measured by the sensor assembly; compare the metric of the pulse wave signal with a plurality of reference metrics of a plurality of reference pulse wave signals; select the blood pressure calculation algorithm from a plurality of reference blood pressure calculation algorithms associated with the plurality of reference pulse wave signals, respectively, based on a result of the comparing; and determine the blood pressure of the subject using the pulse wave velocity of the subject and the selected blood pressure calculation algorithm.

6. The apparatus of claim 5, wherein the sensor assembly comprising an electrocardiography sensor configured to measure an electrocardiography R-wave and a pulse wave sensor configured to measure an arterial pulse wave; the signal processor is configured to calculate a time difference between the electrocardiography R-wave and the arterial pulse wave as a pulse transit time.

7. The apparatus of claim 5, further comprising a memory having a database comprising the plurality of reference metrics corresponding to the plurality of reference blood pressure calculation algorithms; wherein the plurality of reference metrics comprises one or more of a metric in time domain of a reference pulse wave signal, a metric in frequency domain of a reference pulse wave signal, and a metric in time-frequency domain of a reference pulse wave signal.

8. The apparatus of claim 1, wherein the blood pressure calculation algorithm is derived from a prediction model established using a plurality of reference metrics of a plurality of reference pulse wave signals.

9. The apparatus of claim 8, wherein the signal processor is configured to select the prediction model from a plurality of reference prediction models established for a plurality of subpopulations, respectively.

10. A method of determining a blood pressure of a subject, comprising:
  measuring a pulse wave signal of the subject;
  generating a metric of the pulse wave signal;
  determining the blood pressure of the subject using a blood pressure calculation algorithm;
  performing time domain analysis on the pulse wave signal of the subject; and
  performing frequency domain analysis, and time-frequency domain analysis;
  wherein the metric comprises a metric in time domain of the pulse wave signal, a metric in frequency domain of the pulse wave signal, and a metric in time-frequency domain of the pulse wave signal; and
  the metric in time domain of the pulse wave signal comprises at least one of (1) a ratio between amplitudes at two reference points in the time domain of the pulse wave signal; (2) a ratio between Δt1 and Δt2 in the time domain of the pulse wave signal, wherein Δt1 is a first time difference between a first pair of reference points, and Δt2 is a second time difference between a second pair of reference points; or (3) a ratio between S1 and S2, wherein S1 is a first area defined by a first pair of reference points under a curve of a time domain representation of the pulse wave signal, and S2 is a second area defined by a second pair of reference points under the curve of the time domain representation of the pulse wave signal.

11. The method of claim 10, wherein the metric in time domain of the pulse wave signal comprises all of (1) the ratio between amplitudes at two reference points in the time domain of the pulse wave signal; (2) the ratio between Δt1 and Δt2 in the time domain of the pulse wave signal; and (3) the ratio between S1 and S2.

12. The method of claim 10,
  wherein
  the metric in frequency domain of the pulse wave signal comprises a plurality of frequencies with highest energy levels.

13. The method of claim 10,
  wherein
  the metric in time-frequency domain of the pulse wave signal comprises a correlation between a frequency domain metric and a time domain metric.

14. The method of claim 10, further comprising calculating a pulse wave velocity of the subject;
  comparing the metric of the pulse wave signal with a plurality of reference metrics of a plurality of reference pulse wave signals;
  selecting the blood pressure calculation algorithm from a plurality of reference blood pressure calculation algorithms associated with the plurality of reference pulse wave signals, respectively, based on a result of the comparing; and
  determining the blood pressure of the subject using the pulse wave velocity of the subject and the blood pressure calculation algorithm.

15. The method of claim 14, wherein the step of calculating the pulse wave velocity comprises calculating a time difference between an electrocardiography R-wave and an arterial pulse wave as a pulse transit time.

16. The method of claim 10, further comprising establishing a database comprising the plurality of reference metrics corresponding to the plurality of reference blood pressure calculation algorithms; wherein the plurality of reference metrics comprises one or more of a metric in time domain of a reference pulse wave signal, a metric in frequency domain of a reference pulse wave signal, and a metric in time-frequency domain of a reference pulse wave signal.

17. The method of claim 10, wherein the blood pressure calculation algorithm is derived from a prediction model established using a plurality of reference metrics of a plurality of reference pulse wave signals.

18. The method of claim 17, further comprising selecting the prediction model from a plurality of reference prediction models established for a plurality of subpopulations, respectively.

\* \* \* \* \*